United States Patent [19]
Amundson

[11] Patent Number: 5,779,732
[45] Date of Patent: Jul. 14, 1998

[54] METHOD AND APPARATUS FOR IMPLANTING A FILM WITH AN EXANDABLE STENT

[75] Inventor: Rodney R. Amundson, Lindstrom, Minn.

[73] Assignee: Medtronic, Inc., Minneapolis, Minn.

[21] Appl. No.: 829,576

[22] Filed: Mar. 31, 1997

[51] Int. Cl.$^6$ .................................................. A61M 29/00
[52] U.S. Cl. .......................... 606/198; 623/1; 623/12
[58] Field of Search ............................ 606/1, 108, 191, 606/194, 195, 198, 200; 623/1, 12

[56] References Cited

U.S. PATENT DOCUMENTS

| | | |
|---|---|---|
| 4,886,062 | 12/1989 | Wiktor . |
| 5,059,211 | 10/1991 | Stack et al. . |
| 5,078,726 | 1/1992 | Kreamer . |
| 5,123,917 | 6/1992 | Lee ................................ 623/1 |
| 5,219,355 | 6/1993 | Parodi et al. . |
| 5,246,445 | 9/1993 | Yachia et al. . |
| 5,282,823 | 2/1994 | Schwartz et al. . |
| 5,383,928 | 1/1995 | Scott et al. . |
| 5,443,496 | 8/1995 | Schwartz et al. . |
| 5,507,711 | 4/1996 | Gianturco ...................... 606/198 |
| 5,556,413 | 9/1996 | Lam . |
| 5,667,523 | 9/1997 | Bynon et al. ................... 606/198 |
| 5,700,285 | 12/1997 | Myers et al. ................... 606/198 |
| 5,707,385 | 1/1998 | Williams ........................ 606/198 |

FOREIGN PATENT DOCUMENTS 9112779  5/1991  WIPO .

*Primary Examiner*—William Lewis
*Attorney, Agent, or Firm*—Kevin W. Raasch; Dianne M. F. Plunkett; Harold R. Patton

[57] ABSTRACT

Methods and apparatus for implanting a radially expandable stent and separate film within a body vessel. The film is separate from the stent and releasably retained thereon during advancement of the stent to the body vessel. Some methods according to the present invention include steps of providing a collapsed, radially expandable stent; providing a film that is separate from the stent, the film being provided in sheet form; wrapping the film around at least a portion of the stent; and releasably securing the film around the stent with at least one suture or by releasably attaching the first end of the film to a second end of the film. The apparatus according to the present invention include a collapsed, radially expandable stent and a film separate from the stent. The film is releasably attached around the stent by a suture or by releasably attaching the first end of the film to the second end of the film.

19 Claims, 3 Drawing Sheets

METHOD AND APPARATUS FOR IMPLANTING A FILM WITH AN EXANDABLE STENT

FIELD OF THE INVENTION

The present invention relates to intravascular stent implants for maintaining vascular patency in humans and animals and more particularly to a method and apparatus for implanting a film with an expandable stent.

BACKGROUND OF THE INVENTION

Percutaneous transluminal coronary angioplasty (PTCA) is used to reduce arterial build-up of cholesterol fats or atherosclerotic plaque. Typically a first guidewire of about 0.038 inches in diameter is steered through the vascular system to the site of therapy. A guiding catheter, for example, can then be advanced over the first guidewire to a point just proximal of the stenosis. The first guidewire is then removed. A balloon catheter on a smaller 0.014 inch diameter second guidewire is advanced within the guiding catheter to a point just proximal of the stenosis. The second guidewire is advanced into the stenosis, followed by the balloon on the distal end of the catheter. The balloon is inflated causing the site of the stenosis to widen. The dilatation of the occlusion, however, can form flaps, fissures and dissections which threaten reclosure of the dilated vessel or even perforations in the vessel wall. Implantation of a metal stent can provide support for such flaps and dissections and thereby prevent reclosure of the vessel or provide a patch repair for a perforated vessel wall until corrective surgery can be performed. Reducing the possibility of restenosis after angioplasty reduces the likelihood that a secondary angioplasty procedure or a surgical bypass operation will be necessary.

An implanted prosthesis such as a stent can preclude additional procedures and maintain vascular patency by mechanically supporting dilated vessels to prevent vessel collapse. Stents can also be used to repair aneurysms, to support artificial vessels as liners of vessels or to repair dissections. Stents are suited to the treatment of any body lumen, including the vas deferens, ducts of the gallbladder, prostate gland, trachea, bronchus and liver. The body lumens range in size from small coronary vessels to 28 mm in the aortic vessel. The invention applies to acute and chronic closure or reclosure of body lumens.

A typical stent is a cylindrically shaped wire formed device intended to act as a permanent prosthesis. A typical stent can range from 5 mm to 150 mm in length. A stent is deployed in a body lumen from a radially compressed configuration into a radially expanded configuration which allows it to contact and support a body lumen. The stent can be made to be radially self-expanding or expandable by the use of an expansion device. The self expanding stent is made from a resilient springy material while the device expandable stent is made from a material which is plastically deformable. A plastically deformable stent can be implanted during a single angioplasty procedure by using a balloon catheter bearing a stent which has been crimped onto the balloon. Stents radially expand as the balloon is inflated, forcing the stent into contact with the body lumen thereby forming a supporting relationship with the vessel walls.

Conventional angioplasty balloons fall into high, medium and low pressure ranges. Low pressure balloons are those which fall into rated burst pressures below 6 atm. Medium pressure balloons are those which fall into rated burst pressures between 6 and 12 atm. High pressure balloons are those which fall into rated burst pressures above 12 atm. Burst pressure is determined by wall thickness and tensile strength.

The biocompatible metal stent props open blocked coronary arteries, keeping them from reclosing after balloon angioplasty. A balloon of appropriate size and pressure is first used to open the lesion. The process is repeated with a stent crimped on a second balloon. The second balloon may be a high pressure type of balloon, e.g., more than 12 atmospheres, to insure that the stent is fully deployed upon inflation. The stent is deployed when the balloon is inflated. The stent remains as a permanent scaffold after the balloon is withdrawn. A high pressure balloon is preferable for stent deployment because the stent must be forced against the artery's interior wall so that it will fully expand thereby precluding the ends of the stent from hanging down into the channel encouraging the formation of thrombus.

U.S. Pat. No. 5,282,823 to Schwartz et al. for "Intravascularly Radially Expandable Stent" discloses a plurality of metal elements joined to allow flexing of the cylindrical body along the longitudinal axis of the body and a polymeric film extending between the metal elements of the stent. The polymeric film and the wires forming the stent are integrally attached with the film being formed on and around the wires. The polymeric film in such applications is helpful to secure flaps and dissections in place following angioplasty and to patch perforations in the vessel wall.

Therapeutic substances may also be incorporated in the film or on its surfaces such as is described in published International Patent Application WO 91/12779 "Intraluminal Drug Eluting Prosthesis," which is hereby incorporated by reference. The polymeric film can then be used to administer therapeutic substances to the vessel and/or to the bloodstream to, for example, prevent thrombosis or restenosis in the blood vessel.

One problem with stents including an integral or attached film is that it can be expensive to test the use of new film materials for the films or new therapeutic substances provided in or on the films because stents must be specially manufactured with films of the materials to be tested and then implanted in a test subject. These small batches of specially-manufactured stents can increase the costs of testing new materials as well as the time required to obtain test results.

U.S. Pat. No. 5,383,928 to Scott et al. discloses another stent used in combination with a polymer sheath for local delivery of drugs within a body lumen. The sheath can be provided as a sleeve, ring, single or multiple strips, or a polymer coating. Potential disadvantages of the disclosed stent and polymer film combinations is that full expansion of the stent may be inhibited, particularly in those embodiments in which the polymer film is provided as a sleeve or when the polymer film is used to line a graft. Alternatively, where the film is provided as a sleeve, it may tear during expansion of the stent.

In addition, Scott et al. do not discuss methods or apparatus for delivering the stents and polymer films to locations within the body lumens of a patient in detail.

In view of the above, a need exists for an apparatus and method of implanting a separate film in a body vessel using an expandable stent that is both economical and capable of being produced in a relatively short period of time.

SUMMARY OF THE INVENTION

The present invention provides methods and apparatus for implanting a film in a body vessel using a stent. The film is separate from the stent and releasably retained thereon during advancement of the stent to the body vessel.

Advantages of the invention include the ability to implant films that are delivered and retained in place in a body vessel by stents without requiring that the stents be manufactured with integrally-formed films. As a result, the ability of the stents to completely expand during deployment is not inhibited by the polymer film (as is possible if the film were supplied as a sleeve). Furthermore, the films are less likely to tear during deployment because they are not integrally connected to the stent.

Another advantage is that the present invention also provides methods and apparatus for rapid construction and deployment of different stent and polymer film combinations. As a result, the methods and apparatus of the present invention can offer the opportunity to individualize treatment at the point of use by allowing the user to select the polymer film with a desired therapeutic substance for implantation with a stent. This ability to rapidly combine stents and films also provides advantages where it is desired to test new materials and/or the delivery of new therapeutic substances in the films.

In one aspect, the methods according to the present invention include steps of providing a collapsed, radially expandable stent; providing a film that is separate from the stent, the film being provided in sheet form; wrapping the film around at least a portion of the stent; and releasably securing the film around the stent with at least one suture.

In another aspect, the methods according to the present invention include steps of providing a collapsed, radially expandable stent; providing a film that is separate from the stent, the film being provided in sheet form; wrapping the film around at least a portion of the stent; and releasably securing the film around the stent by releasably attaching a first end of the film to a second end of the film.

In one aspect, the apparatus according to the present invention include a collapsed, radially expandable stent; a film separate from the stent, the film being wrapped around at least a portion of the stent; and a suture releasably securing the film around the stent.

In another aspect, the apparatus according to the present invention include a collapsed, radially expandable stent; a film separate from the stent, the film being wrapped around at least a portion of the stent; wherein a first end of the film is releasably attached to a second end of the film.

These and other features and advantages of the methods and apparatus according to the present invention are discussed in greater detail below with reference to the figures.

DETAILED DESCRIPTION OF THE PREFERRED EMBODIMENTS

The present invention provides both methods and apparatus for implanting a film within a body vessel using a stent. The ability to deliver and maintain a separate film in place within a body vessel with a stent provides a number of advantages, including in vivo testing of new films and materials for use in body vessels, particularly when used for testing in non-human body vessels.

The apparatus and methods according to the present invention can be used with any radially expandable stent, including stents that are expanded by actuators (such as balloons), as well as stents that are self-expanding from a collapsed or unexpanded configuration. Examples of suitable stents for use in connection with the present invention are described in U.S. Pat. Nos. 4,886,062 to Wiktor (balloon expandable) and 5,246,445 to Yachia et al. (self-expanding), both of which are hereby incorporated by reference.

The apparatus and methods are useful for implanting or locating a film in vivo using a stent to maintain the film in the desired position. The films should be capable of being wrapped around the stent to prevent a low profile—thereby allowing transluminal delivery of the film-wrapped stent to the desired location. It is preferred that the films be provided in a flat configuration, i.e., non-tubular to assist in wrapping the film over the stent with a low profile. Typically, the films will be rectangular in shape, although films with non-rectangular shapes could also be used. Also, the film is preferably shorter than the stent (in the longitudinal direction) to prevent the ends of the film from obstructing the open ends of the stents.

The materials used for the films can include any desired material, although the resulting film should have sufficient flexibility to allow for wrapping the film over the stent as well as the subsequent expansion of the stent in a body vessel. The films can be porous or non-porous and also may be impregnated or coated with one or more therapeutic substances.

Figure 1:
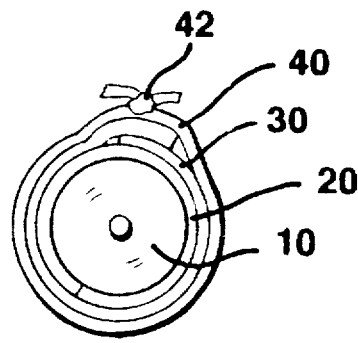
FIG. 1 is an end view of one apparatus including a stent and a separate film according to the present invention, the stent being collapsed and located over a deflated balloon catheter.
Figure 2:
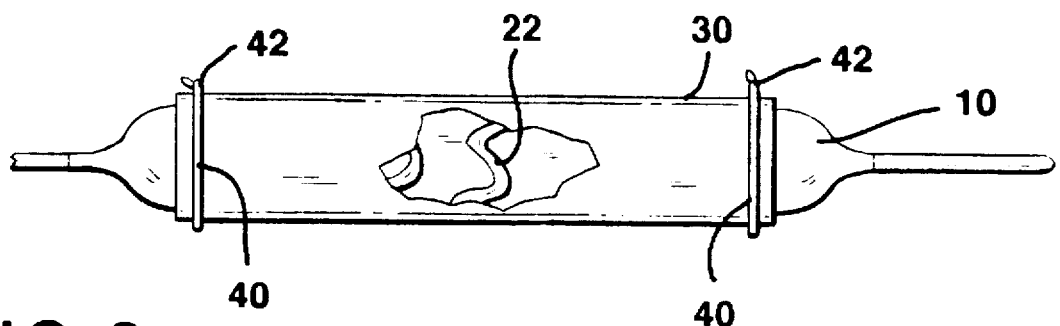
FIG. 2 is a side elevation of the apparatus of FIG. 1, with a portion of the film being cut-away to reveal the underlying stent.
Figure 3:
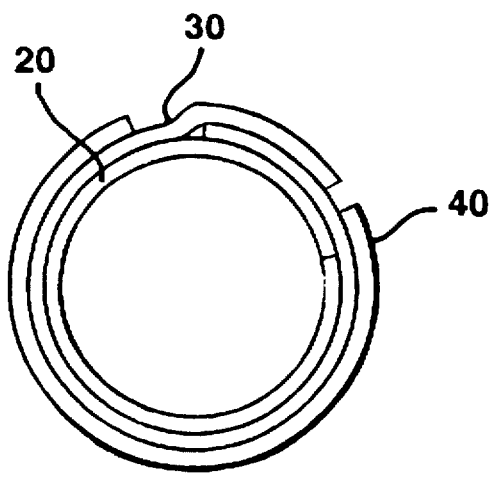
FIG. 3 is an end view of the apparatus of FIG. 1 after the stent has been expanded radially.

Referring now to FIGS. 1–3, one apparatus including a stent and a separate film will be described along with a method for using the apparatus according to the present invention. The apparatus includes a stent 20 that must be expanded by an actuator. The stent 20 is located over a collapsed balloon catheter 10 which functions as the actuator required to expand the stent 20. FIGS. 1 and 2 depict the balloon 10 and stent 20 in a collapsed or unexpanded state.

A separate film 30 is wrapped over the stent 20 and includes a first end and a second end preferably overlapping the first end of the film. By "separate" as used in connection with the films in the present invention, it is meant that the film 30 is not provided integrally attached to the stent 20 in the way that known stents incorporating films are integrally attached or molded together (such as those described in U.S. Pat. No. 4,886,062 to Wiktor). Rather, the film 30 is only wrapped over the stent 20 and the film 30 itself does not completely enclose any portion of the stent 20, e.g., the wires 22 (see FIG. 2) that make up the stent 20 are not molded into the film 30 nor is the film 30 formed around the stent wires 22. As a result, the film 30 does not constrain expansion of the stent 20 during deployment (after the mechanism used to retain the film 30 in place on the stent 20 has been released).

The film 30 is releasably retained in place over the collapsed stent 20 to allow placement of the film 30 and stent 20 in a desired location in a body vessel. Typically, the stent 20 and film 30 will be introduced percutaneously. When the stent 20 and film 30 are in the desired location, the stent 20 is expanded radially to force the film 30 against a vessel wall or other tissue surrounding the stent 20. As a result, the film 30 will preferably be held in position within the body vessel by the force of the stent 20. The apparatus depicted in FIGS. 1–3 includes one mechanism for releasably retaining the film 30 in place over stent 20 before the stent 20 is expanded. Some additional mechanisms are depicted in FIGS. 4–7 and described below. Those skilled in the art will however, recognize that many other mechanisms and/or systems for releasably retaining a separate film over an expandable stent may be provided in place of the specific embodiments described herein.

As depicted in FIGS. 1 and 2, one mechanism for releasably retaining the film 30 over the stent 20 includes sutures 40 tied around the combination of catheter 10, stent 20 and film 30. The ends of the suture 40 are preferably tied together in a manner that will open or release as the underlying stent 20 is expanded radially. One example of such a knot is a slip knot 42. Other knots will be known to those skilled in the art.

The apparatus of FIGS. 1 and 2 is shown after radial expansion of the stent 20 in the end view of FIG. 3. The ends of one of the sutures 40 are shown pulled apart by the expansion of the stent 20 and film 30 in FIG. 3. The sutures 40 may be of the type that are absorbed or otherwise disintegrate over time or they may be made of a material, e.g., polypropylene, that is not absorbed.

In addition to providing a knot 42 that allows the stent 20 and film 30 to expand radially by pulling the ends of the suture 40 apart, other variations such as providing sutures 40 that break or rupture upon expansion of the stent 20 could be provided to releasably retain the film 30 on the stent 20 before expansion. Likewise, the sutures 40 could be adhesively attached or welded (ultrasonic or otherwise) to the surface of the film 30 rather than tied together to releasably retain the film 30 on the stent 20.

Figure 4:
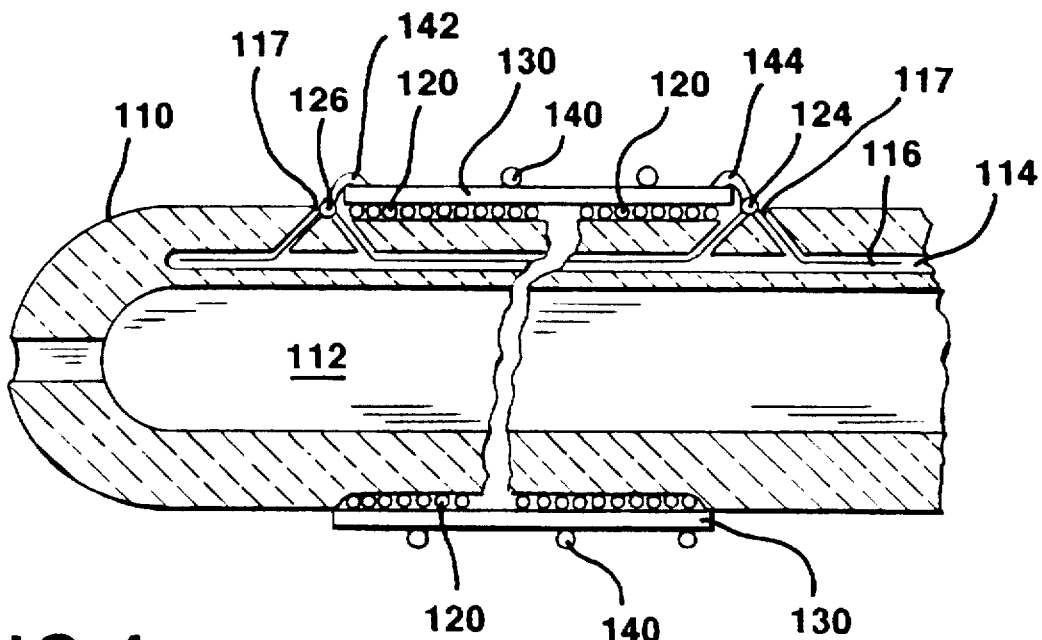
FIG. 4 is a cross-sectional side view of another apparatus including a self-expanding stent and separate film according to the present invention, the stent being collapsed over a delivery device.

Turning now to FIG. 4, another embodiment of an apparatus according to the present invention is depicted. The apparatus includes a stent 120 located on a tube 110. The stent 120 is preferably of the self-expanding type such as, e.g., those described in U.S. Pat. No. 5,246,445 to Yachia et al. The tube 110 preferably includes a primary lumen 112 adapted to receive a guidewire to assist in delivery of the stent 120 to the desired location in a body vessel. The tube 110 also preferably includes a second lumen 114 enclosing an elongated retaining device 116 (typically a wire and referred to below as such). The wire 116 extends through openings 117 in the tube 110 to retain the proximal end 124 and distal end 126 of the stent 120 against the tube 110, thereby retaining the stent 120 in a collapsed or unexpanded configuration. Further details regarding the construction and manufacturing of the tube 110 and stent 120 can be found in the patent referenced above.

Like the apparatus depicted in FIGS. 1 and 2, the apparatus in FIG. 4 also includes a separate film 130 wrapped over the stent 120. The film 130 is releasably retained in place over the collapsed stent 120 to allow placement of the film 130 and stent 120 in a desired location in a body vessel.

Typically, the stent 120 and film 130 will be introduced percutaneously. When the stent 120 and film 130 are in the desired location, the stent 120 is expanded radially to force the film 130 against a vessel wall or other tissue surrounding the stent 120. As a result, the film 130 will preferably be held in position by the stent 120.

The apparatus depicted in FIG. 4 includes another mechanism for releasably retaining the film 130 in place over stent 120 before the stent 120 is expanded. As shown, the mechanism includes a suture 140 that is helically wound around the stent 120 and film 130. A first end 142 of the suture 140 is attached proximate the distal end 126 of the stent 120 while a second end 144 of the suture 140 can be attached proximate the proximal end 124 of the stent 120. It is preferred that the suture 140 be attached such that as the stent 120 is released using wire 116, the suture 140 is also released such that the stent 120 and film 130 expand together.

In the apparatus of FIG. 4, for example, it is preferred that the first end 142 of the suture 140 be attached such that the first end of suture 140 releases when the distal end 126 of the stent 120 is released when wire 116 is withdrawn through lumen 114 in tube 110. Likewise, it is preferred that the second end 144 of the suture 140 be released as the proximal end 124 of the stent 120 is released when wire 116 is withdrawn through the lumen 114. The suture 140 be retained by either the tube 110 or wire 116 such that as the tube 110 is removed after the stent 120 is expanded, the suture 140 can also be removed from the location of the stent 120 and film 130. Alternatively, the suture 140 can remain in place between the film 130 and body vessel.

In another variation of the apparatus depicted in FIG. 4, it will be understood that two sutures (not shown) could be supplied with a suture wound around the film 130 and attached to the release wire 116 or other structure such that as the stent 120 is released, the sutures also release. Alternatively, the sutures may not be attached to the stent release mechanisms, but rather be provided with slip knots or other mechanisms as discussed above with respect to the apparatus of FIGS. 1–3 that allow the film 130 to expand when the stent 120 expands.

Figure 5:
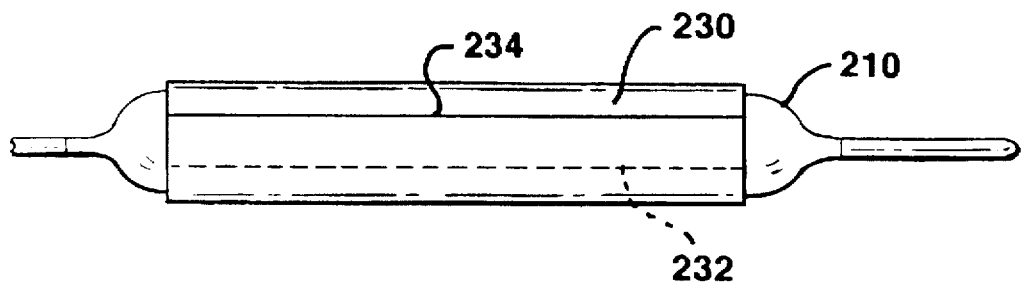
FIG. 5 is a side elevation of another apparatus including a stent and a separate film according to the present invention, the stent being collapsed and located over a deflated balloon catheter.
Figure 6:
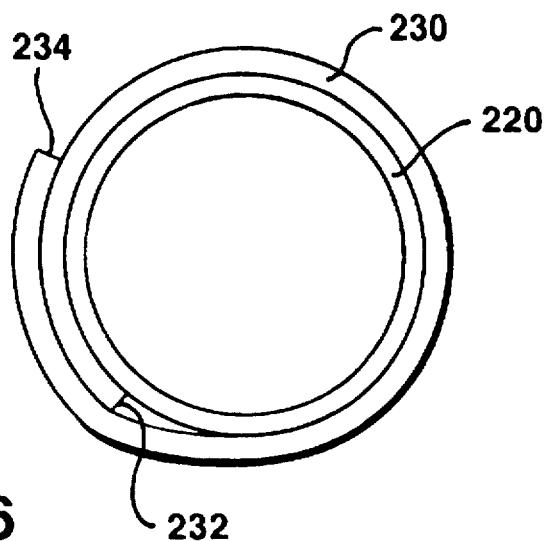
FIG. 6 is an end view of the apparatus of FIG. 5.

FIGS. 5 and 6 depict another apparatus according to the present invention. The apparatus includes a stent 220 that must be expanded by an actuator. The stent 220 is located over a collapsed balloon catheter 210 which functions as the actuator required to expand the stent 220. FIGS. 5 and 6 depict the balloon 210 and stent 220 in a collapsed or unexpanded state.

A separate film 230 is wrapped over the stent 220 and includes a first end 232 and a second end 234 preferably overlapping the first end of the film 232. The film 230 is releasably retained in place over the collapsed stent 220 to allow placement of the film 230 and stent 220 in a desired location in a body vessel. Typically, the stent 220 and film 230 will be introduced percutaneously. When the stent 220 and film 230 are in the desired location, the stent 220 is expanded radially to force the film 230 against a vessel wall or other tissue surrounding the stent 220. As a result, the film 230 will preferably be held in position within the body vessel by the stent 220.

The apparatus depicted in FIGS. 5 and 6 includes another mechanism for releasably retaining the film 230 in place over stent 220 before the stent 220 is expanded. That mechanism involves attaching the second end 234 of the film 230 to the first end 232 in the area where the two ends overlap. The exact mechanism used may vary, but examples include adhesives and welding (through ultrasonic energy or otherwise), but will typically involve attaching the ends of the film 230 together with sufficient strength to ensure that the film 230 is retained in place on the stent 220 during the delivery process, but not strong enough to prevent the stent 220 from expanding radially when desired.

Figure 7:
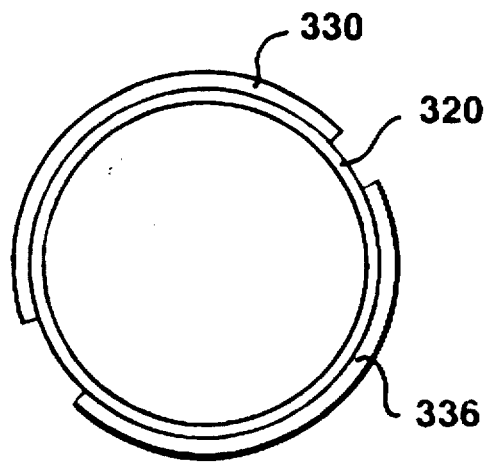
FIG. 7 is an end view of an expanded stent having two films located about its circumference.

In another variation, the present invention can also provide an apparatus and method of delivering two or more different films as depicted in FIG. 7. The apparatus includes a stent 320 (shown as expanded) around which two films 330 and 336 are located. The stent 320 and films 330 and 336 could be delivered by any of the various apparatus depicted in FIGS. 1-6 and described above.

Figure 8:
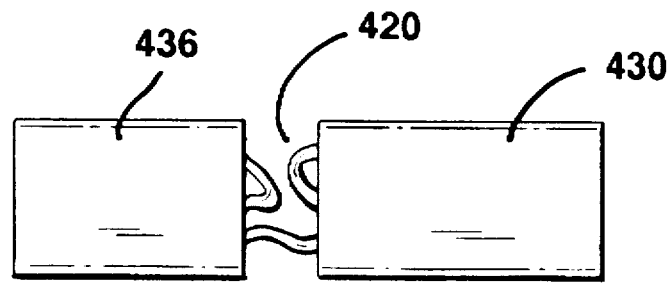
FIG. 8 is a side elevation of another apparatus according to the present invention with two films spaced longitudinally along an expanded stent.

In yet another variation depicted in FIG. 8, the apparatus and methods of the present invention can be used to deliver two or more films 430 and 436 that are displaced axially along a stent 420 (or stents—not shown).

The preceding specific embodiments are illustrative of the practice of the invention. It is to be understood, however, that other expedients known to those skilled in the art or disclosed herein, may be employed without departing from the scope of the appended claims.

| No. | Component |
| --- | --- |
| 10 | Balloon Catheter |
| 20 | Stent |
| 22 | Stent Wires |
| 30 | Film |
| 40 | Sutures |
| 42 | Knot |
| 110 | Tube |
| 112 | Primary Lumen |
| 114 | Second Lumen |
| 116 | Retaining Wire |
| 117 | Openings in Tube 110 |
| 120 | Stent |
| 124 | Proximal End of Stent 120 |
| 126 | Distal End of Stent 120 |
| 130 | Film |
| 140 | Suture |
| 142 | First End of Suture 140 |
| 144 | Second End of Suture 140 |
| 210 | Balloon Catheter |
| 220 | Stent |
| 230 | Film |
| 232 | First End of Film 230 |
| 234 | Second End of Film 230 |
| 320 | Stent |
| 330 | First Film |
| 336 | Second Film |
| 420 | Stent |
| 430 | First Film |
| 436 | Second Film |

What is claimed is:

1. A method for manufacturing a film-wrapped stent, the method comprising steps of:
   providing a collapsed, radially expandable stent;
   providing a film that is separate from the stent, the film being provided in sheet form and having first and second ends;
   wrapping the film around at least a portion of the stent; and
   releasably securing the film around the stent with at least one suture extending about the exterior of the film.

2. A method according to claim 1, wherein the ends of the suture are tied together.

3. A method according to claim 1, comprising providing at least two sutures about the film, wherein the ends of each suture are tied together.

4. A method according to claim 1, wherein one end of the suture is attached to a proximal end of a stent release mechanism and the other end of the stent is attached to a distal end of the stent release mechanism.

5. A method according to claim 4, wherein the suture coils about the film and stent.

6. A method according to claim 1, wherein the step of wrapping the film comprises wrapping the film about the stent wherein the first and second ends of the film overlap.

7. A method for manufacturing a film-wrapped stent, the method comprising steps of:
   provided a collapsed, radially expandable stent;
   providing a film that is separate from the stent, the film being provided in sheet form and having first and second ends;
   wrapping the film around at least a portion of the stent; and
   releasably securing the film around the stent by releasably attaching the first end of the film to the second end of the film.

8. A method according to claim 7, wherein the step of releasably attaching the first end of the film to the second end of the film comprises adhesively attaching the first and second ends of the film together.

9. A method according to claim 7, wherein the step of releasably attaching the first end of the film to the second end of the film comprises welding the first and second ends of the film together.

10. A method according to claim 7, wherein the step of wrapping the film comprises wrapping the film about the stent wherein the first and second ends of the film overlap.

11. A radially expandable stent apparatus comprising:
   a collapsed, radially expandable stent;
   a film separate from the stent, the film being wrapped around at least a portion of the stent, the film being provided in sheet form and having first and second ends; and
   a suture releasably securing the film around the stent, the suture extending about the exterior of the film.

12. An apparatus according to claim 11, wherein the ends of the suture are tied together.

13. An apparatus according to claim 11, wherein the suture is located proximate a distal end of the stent and another suture is located proximate a proximal end of the stent.

14. An apparatus according to claim 11, wherein the stent includes a release mechanism, and further wherein one end of the suture is attached to a proximal end of the stent release mechanism and the other end of the suture is attached to a distal end of the stent release mechanism.

15. An apparatus according to claim 11, wherein the first end of the film overlaps the second end of the film.

16. An apparatus for placing a film in a body vessel, the apparatus comprising:
   a collapsed, radially expandable stent; and
   a film separate from the stent, the film being provided in sheet form having first and second ends, the film being wrapped around at least a portion of the stent; wherein the first end of the film is releasably attached to the second end of the film.

17. An apparatus according to claim 16, further comprising an adhesive between the first and second ends of the film.

18. An apparatus according to claim 16, wherein the first end of the film is welded to the second end of the film.

19. An apparatus according to claim 16, wherein the first end of the film overlaps the second end of the film.

* * * * *